United States Patent [19]

Pendery et al.

[11] Patent Number: 4,475,000

[45] Date of Patent: Oct. 2, 1984

[54] PROCESS FOR PRODUCING 4,4'-DIHYDROXYBIPHENYL

[75] Inventors: John J. Pendery, Huntington Woods; James G. Jolly, Lathrup Village, both of Mich.

[73] Assignee: Ethyl Corporation, Richmond, Va.

[21] Appl. No.: 469,724

[22] Filed: Feb. 25, 1983

Related U.S. Application Data

[63] Continuation-in-part of Ser. No. 459,783, Jan. 21, 1983, abandoned.

[51] Int. Cl.$^3$ ............................................. C07C 39/14
[52] U.S. Cl. ................................................... 568/730
[58] Field of Search ......................................... 568/730

[56] References Cited

U.S. PATENT DOCUMENTS 4,340,768  7/1982  Jinbo et al. .......................... 568/730

FOREIGN PATENT DOCUMENTS 1930341  12/1970  Fed. Rep. of Germany ...... 568/730
54-22347  2/1979  Japan .................................. 568/730

*Primary Examiner*—Werren B. Lone
*Attorney, Agent, or Firm*—Donald L. Johnson; John F. Sieberth; Teresa M. Stanek

[57] ABSTRACT

A process for the preparation of 4,4'-dihydroxybiphenyl by hydrolyzing 4,4'-dibromobiphenyl in the presence of a copper compound catalyst containing copper in the plus two oxidation state. The process involves only one extraction.

10 Claims, No Drawings

PROCESS FOR PRODUCING 4,4'-DIHYDROXYBIPHENYL

CROSS REFERENCE TO RELATED APPLICATION

This application is a continuation-in-part of application Ser. No. 459,783, filed Jan. 21, 1983 now abandoned.

BACKGROUND OF THE INVENTION

1. Field of the Invention

The present invention is directed to the preparation of 4,4'-dihydroxybiphenyl. More particularly, this invention involves the hydrolysis of 4,4'-dibromobiphenyl in the presence of a copper compound catalyst.

2. Description of the Prior Art 4,4'-Dihydroxybiphenyl is useful as an antioxidant for a resin, an intermediate for a dye and a starting material for polyesters, polyepoxides, polyurethanes and polycarbonates. It may also be used as a co-monomer in high performance polyester film, cable, rope and engineering plastics.

U.S. Pat. No. 4,340,768 teaches the production of 4,4'-dihydroxybiphenyl by hydrolyzing 4,4'-dibromobiphenyl in the presence of a copper compound catalyst in an aqueous solution, extracting by-products from the alkaline aqueous solution with an alcohol or ketone which forms an organic phase, neutralizing or acidifying the alkaline aqueous solution with an acid, extracting the reaction product with the alcohol or ketone and finally crystallizing the reaction product from the extracted solution. This process requires two extractions using an alcohol or ketone. The first extraction is designed to remove by-products impurities.

It has recently been discovered that by using a copper compound catalyst containing copper in the plus two oxidation state minimal by-products are formed in the hydrolysis reaction and lesser amounts of catalyst are required.

SUMMARY OF THE INVENTION

According to the present invention, 4,4'-dihydroxybiphenyl having high purity can be prepared by hydrolyzing 4,4'-dibromobiphenyl in the presence of a copper compound catalyst containing copper in the plus two oxidation state in an alkaline aqueous solution, separating said copper compound catalyst from said alkaline aqueous solution, acidifying said alkaline aqueous solution with an acid forming a solid, separating said solid, dissolving said solid in an inert organic solvent leaving an inorganic salt, separating said inorganic salt, and distilling the resultant solution to remove solvents and residual water.

DESCRIPTION OF THE PREFERRED EMBODIMENTS

In accordance with the present invention, 4,4'-dihydroxybiphenyl having high purity can be prepared by hydrolyzing 4,4'-dibromobiphenyl in the presence of a copper compound catalyst containing copper in the plus two oxidation state in an alkaline aqueous solution.

The reaction is carried out in an autoclave filled with either $N_2$ and air. Similar results are obtained in either system. However, preferred reaction times and temperatures are generally decreased in an air environment.

The copper compound catalyst used in the practice of the present invention is in a plus two oxidation state. Typical catalysts include a copper chelate, a cupric halide such as copper bromide or copper chloride, copper acetate, copper citrate, copper sulfate, cupric tartrate, and the like. A desirable copper compound catalyst in the practice of the present invention is copper sulfate. The copper catalyst precipitates from solution after the hydrolysis reaction and is filtered out.

The amount of catalyst used in the practice of the present invention varies depending on the reaction conditions selected. The amount of catalyst should be sufficient to hydrolyze 4,4'-dibromobiphenyl to 4,4'-dihydroxybiphenyl. The amount of catalyst used is oftentimes within the range of about 0.1 to about 5.0 weight percent of the 4,4'-dibromobiphenyl charged. More preferably, the amount of catalyst is within the range of about 0.5 to about 2.0 weight percent of the 4,4'-dibromobiphenyl charged.

The hydrolysis initially occurs in an alkaline aqueous medium. Any alkali metal hydroxide can used to obtain a suitable alkaline medium. Typical alkaline hydroxides include sodium hydroxide, lithium hydroxide, potassium hydroxide, and the like. The pH is greater than 7. The amount of base used is in stoichiometric excess of that required to neutralize the solution. Generally, the pH is within the range of about 9 to 14.

The hydrolysis generally begins at room temperature and the system is gradually heated up to about 300° C. Oftentimes, the temperature is within the range of 200° to 300° C. More preferably, the temperature is within the range of 250° to 300° C.

Reaction time varies depending on the conditions selected and the desired conversion. The reaction time generally ranges from 1 hour to 3 hours. Preferably, the reaction time ranges from 1 to 2 hours.

The alkaline aqueous solution containing the 4,4'-dihydroxybiphenyl product is then acidified with an acid. The pH of the solution is less than 7.0. Any type of acid may be used in the practice of the present invention. Typical acids include hydrochloric acid, hydrobromic acid, sulfuric acid, phosphoric acid, hydroiodic acid, acetic acid, and the like. The preferred acid is hydrobromic acid. The desired product precipitates out of solution and is filtered.

At this point the solid product is dissolved in an inert organic solvent in which the solid 4,4'-dihydroxybiphenyl is soluble and inorganic salts are either insoluble or slightly soluble. The inorganic salts such as sodium sulfate, sodium bromide and the like may be removed by filtration, centrifuging or in a similar manner. Typical organic solvents include carboxylic acid esters, such as methyl acetate, ethyl acetate, amyl acetate, methyl propionate, ethyl propionate, methyl butyrate, methyl hexanoate, methyl heptanoate, methyl oleate, methyl linoleate, methyl stearate and other acid esters having three to eighteen carbon atoms, also ethers and cyclic ethers, such as diethyl ether, tetrahydrofuran, dioxane, and the like, poly(ethylene glycol) ethers, such as ethylene glycol monomethyl ether, ethylene glycol dimethyl ether, diethylene glycol monomethyl ether, diethylene glycol dimethyl ether, triethylene glycol monoethyl ether, triethylene glycol dimethyl ether, polyethylene glycol monoethyl ether, polyethylene glycol dimethyl ether, and the like.

The preferred organic solvent is an alcohol or a ketone. Suitable alcohols include methanol, ethanol, propanol, isopropanol, 1-butanol, 2-butanol, isobutanol, 1-pentanol, 2-pentanol, 1-hexanol, 1-heptanol, 2-heptanol, 1-octanol, 2-ethyl-1-hexanol, cyclohexanol, cyclopentanol, n-amyl alcohol, isoamyl alcohol, t-amyl alcohol, neopentyl alcohol, capryl alcohol, n-decyl alcohol, ethylene glycol, 1,2-propanediol (dl), 1,3-propanediol, 1,3-butanediol (dl), 1,4-butanediol, 2,3-butanediol (mixt.), 1,5-pentanediol, glycerol, and the like.

Suitable ketones include acetone, 2-hexanone, methyl isobutyl ketone, 2-heptanone, 4-heptanone, diisobutyl ketone, mesityl oxide, phorone, isophorone, cyclohexanone, acetophenone, methyl cyclohexanone, methyl ethyl ketone, methyl n-propyl ketone, diethyl ketone, hexanone-2, hexanone-3, methyl t-butyl ketone, di-n-propyl ketone, diisopropyl ketone, di-n-amyl ketone, and the like. The more preferred organic solvents are acetone and isopropanol.

The remaining solution containing the 4,4'-dihydroxybiphenyl product may optionally be diluted with an aromatic hydrocarbon such as toluene, xylene, monochlorobenzene, and the like, or an aliphatic hydrocarbon such as n-hexane, ligroin and the like. The preferred hydrocarbon solvent for this dilution is toluene. The amount of hydrocarbon solvent used varies over a wide range depending on the water content. The purpose of the solvent is to azeotrope out the water producing a dry product.

The present invention is further illustrated by the following examples which are provided for purposes of illustration only and are not intended to limit the present invention.

EXAMPLES

A 600 ml autoclave was charged with 400 ml of 1N NaOH (0.4 mole), 11.5 g (37 mmole) 4,4'-dibromobiphenyl and 64 mg (0.256 mmole) CuSO$_4$.5H$_2$O as 4 ml of 0.064M solution in H$_2$O. The autoclave was pressure checked with N$_2$ to 1100 psi, vented, flushed with air and resealed. The autoclave was heated to 300° C. at an autogenic pressure of 1168 psi. These conditions were maintained for two hours. After cooling and venting the aqueous reaction product was filtered to remove a grey solid which probably contained catalyst and unreacted starting material. This filter was then removed to a second filter flask. Any starting material remaining was recovered by washing with acetone and stripping the solvent on a rotary evaporator. The filtered aqueous product solution was acidified (pH2) with 25% sulfuric acid. The precipitated crude biphenol was filtered and washed with water (50 ml). The damp crude biphenyl was dissolved in acetone. The insoluble occluded salts (NaBr and Na$_2$SO$_4$) were filtered and washed with acetone. Biphenol was recovered by diluting the acetone with an equal portion of toluene and then rotary evaporating the acetone, toluene and residual water. The biphenol and recovered starting material were analyzed by gas chromatography.

Any solids filtered from the acetone solution of the crude biphenol, as described above, were added to the acidified aqueous filtrate. This aqueous solution was transferred to a 1 liter flask and diluted with distilled, deionized water. Analysis of this solution by potentiometric titration gave the amount of inorganic bromide. When calculated as a percent of the theoretical amount of bromide, it yields the conversion of the reaction.

The following set of tables identifies 14 separate runs following the above procedure. The reactants and reaction conditions are indicated.

| HYDROXYDEBROMINATION OF 4,4'-DIBROMOBIPHENYL | | | | | | |
|---|---|---|---|---|---|---|
| | Reaction Conditions | | | | | |
| Run | Time (hr.) | Temp (°C.) | Atmosphere | NaOH Conc. | Catalyst Weight (mgms.) | DBB mmoles |
| 1 | 3 | 250 | N$_2$ | 1N | None | 37 |
| 2 | 2 | 300 | N$_2$ | 1N | 64 | 37 |
| 3 | 2 | 300 | N$_2$ | 1N | 640 | 37 |
| 4 | 1 | 250 | air | 1N | 64 | 37 |
| 5 | 1 | 250 | air | 1N | 640 | 37 |
| 6 | 1 | 250 | air | 2N | 640 | 37 |
| 7 | 1 | 298 | air | 1N | 64 | 37 |
| 8 | 1 | 295 | air | 1N | 640 | 37 |
| 9 | 1 | 293 | air | 2N | 64 | 37 |
| 10 | 2 | 300 | air | 1N | 64 | 37 |
| 11 | 1 | 290 | air | 2N | 640 | 37 |
| 12 | 3 | 297 | air | 2N | 640 | 111 |
| 13 | 3 | 300 | air | 4.6N | 1000 | 333 |
| 14 | 1 | 298 | air | 4.6N | 2000 | 333 |

| | | | Analysis | | | | |
|---|---|---|---|---|---|---|---|
| | inorg Br percent | | Crude Yield | melt.pt. | VPC area % | | |
| Run | of Theory | Sample | percent | °C. | Biphenol | BHB | HB | DBB |
| 1 | 47.2 | B | 56.6 | 215-240 | 38.7 | 46.7 | 2.7 | 10.4 |
|   |      | RSM | 18.8 | 145-152 | 13.6 | 78.2 | ND | ND |
| 2 | 97.8 | B | 65 | 210-261 | 67.0 | 27.8 | 2.6 | 0.7 |
| 3 | 99.5 | B | 96 | 274-280 | 97.1 | 0.6 | 2.3 | ND |
| 4 | 88.4 | B | 93.6 | 266-278 | 88.6 | 9.8 | 1.2 | ND |
|   |      | RSM | 4.3 | | | | | |
| 5 | 96.1 | B | 100.7 | 277-278.5 | 95.0 | 0.3 | 2.3 | ND |
| 6 | 98.7 | B | 96.8 | 277-281 | 96.4 | 0.7 | 1.4 | ND |
|   |      | RSM | trace | | 4.8 | 71.5 | 9.1 | ND |
| 7 | 96.1 | B | 95.4 | 245-274 | 80.9 | 17.3 | 1.2 | trace |
| 8 | 99.1 | B | 96.1 | 273-279 | 94.1 | 0.9 | 2.6 | ND |
| 9 | 94.2 | B | 93.6 | 227-264 | 58.6 | 38.2 | 1.2 | 1.7 |
|   |      | RSM | 0.6 | | 2.6 | ND | ND | 68.9 |
| 10 | 96.5 | B | 102 | 263-272 | 90.2 | 6.9 | 1.9 | ND |
| 11 | 98.4 | B | 103 | 272-278 | 94.6 | 1.5 | 2.0 | ND |

-continued
HYDROXYDEBROMINATION OF 4,4'-DIBROMOBIPHENYL

| | | | | | | | | |
|---|---|---|---|---|---|---|---|---|
| | | RSM | 1 | | 1.5 | 7.1 | 5.6 | ND |
| 12 | 94.0 | B | 101 | 272–278 | 93.9 | 0.9 | 4.0 | ND |
| 13 | 95.9 | B | 94.5 | 258–275 | 86.7 | 3.1 | 9.0 | ND |
| | | RSM | | | | | | |
| 14 | 101.6 | B | 94.6 | 262–275 | 91.9 | 1.1 | 6.5 | ND |
| | | RSM | | | 22.7 | ND | 42.4 | ND |

In the above table, DBB is 4,4'-dibromobiphenyl, RSM represents recovered starting material 4,4'-dibromobiphenyl, B is crude 4,4'-dihydroxybiphenol, Biphenol is 4,4'-dihydroxybiphenyl, BHB is 4-bromo-4'-hydroxybiphenyl, HB is 4-hydroxybiphenyl and ND means not detected by vapor phase chromatography.

As indicated by the above table, excellent yields of 4,4'-dihydroxybiphenyl can be obtained and minimal by-products are formed using the process of the present invention.

We claim:

1. A process for the preparation of 4,4'-dihydroxybiphenyl having high purity said process comprising:
   (a) hydrolyzing 4,4'-dibromobiphenyl in the presence of a copper compound catalyst containing copper in the plus two oxidation state selected from the group consisting of a copper chelate, a cupric halide, copper acetate, copper citrate, copper sulfate and cupric tartrate, in an alkaline aqueous solution at a temperature of from room temperature to 300° C.;
   (b) separating said copper compound catalyst from said alkaline aqueous solution;
   (c) acidifying said alkaline aqueous solution with an acid forming a solid;
   (d) separating said solid;
   (e) dissolving said solid in an inert organic solvent in which said solid is soluble and inorganic salts are either insoluble or slightly soluble leaving an inorganic salt residue;
   (f) separating said inorganic salt residue from the organic solution; and
   (g) distilling said organic solution to remove solvents and residual water.

2. A process as recited in claim 1 wherein said inert organic solvent is an alcohol or ketone.

3. A process as recited in claim 2 wherein said catalyst is about 0.1 to about 5.0 weight percent of the 4,4'-dibromobiphenyl charged.

4. A process as recited in claim 3 wherein said copper compound catalyst is copper sulfate.

5. A process as recited in claim 4 wherein said acid is hydrobromic acid.

6. A process for the preparation of 4,4'-dihydroxybiphenyl having high purity said process comprising:
   (a) hydrolyzing 4,4'-dibromobiphenyl in the presence of copper sulfate catalyst in an amount sufficient to hydrolyze said 4,4'-dihydroxybiphenyl to 4,4'-dibromobiphenyl in an alkaline aqueous solution at a temperature of from 200° C. to 300° C.;
   (b) separating said copper sulfate from said alkaline aqueous solution;
   (c) acidifying said alkaline aqueous solution with an acid forming a solid;
   (d) separating said solid;
   (e) dissolving said solid in an alcohol or ketone in which said solid is soluble and inorganic salts are either insoluble or slightly soluble leaving an inorganic salt residue;
   (f) separating said inorganic salt residue from the organic solution; and
   (g) distilling said organic solution to remove solvents and residual water.

7. A process as recited in claim 6 wherein said ketone is acetone.

8. A process as recited in claim 6 wherein said alcohol is isopropanol.

9. A process as recited in claim 6 wherein the temperature ranges from 250° C. to 300° C.

10. A process for the preparation of 4,4'-dihydroxybiphenyl having high purity said process comprising:
    (a) hydrolyzing 4,4'-dibromobiphenyl in the presence of a copper sulfate catalyst in an amount sufficient to hydrolyze said 4,4'-dihydroxybiphenyl to 4,4'-dibromobiphenyl in an alkaline aqueous solution at a temperature of from 250° C. to about 300° C.;
    (b) separating said copper sulfate from said alkaline aqueous solution;
    (c) acidifying said alkaline aqueous solution with hydrobromic acid forming a solid;
    (d) separating said solid;
    (e) dissolving said solid in acetone leaving an inorganic salt residue;
    (f) separating said inorganic salt residue from the organic solution; and
    (g) distilling said organic solution to remove solvents and residual water.

* * * * *